United States Patent
Murthy et al.

[11] Patent Number: 6,101,238
[45] Date of Patent: Aug. 8, 2000

[54] SYSTEM FOR GENERATING A COMPOUND X-RAY IMAGE FOR DIAGNOSIS

[75] Inventors: Sreerama K. Murthy, Monmouth Junction, N.J.; Carol L. Novak, Newtown, Pa.; Jianzhong Qian, Princeton Junction; Zhenyu Wu, Plainsboro, both of N.J.

[73] Assignee: Siemens Corporate Research, Inc., Princeton, N.J.

[21] Appl. No.: 09/200,069

[22] Filed: Nov. 25, 1998

[51] Int. Cl.[7] .................................................. G01N 23/04
[52] U.S. Cl. .............................. 378/62; 378/98; 382/130; 382/132
[58] Field of Search ................... 378/37, 62, 98, 378/98.2; 382/130, 132

[56] References Cited

U.S. PATENT DOCUMENTS

| | | | |
|---|---|---|---|
| 4,970,393 | 11/1990 | Funahashi | 250/327.2 |
| 5,262,856 | 11/1993 | Lippman et al. | 358/136 |
| 5,268,967 | 12/1993 | Jang et al. | 382/386 |
| 5,575,286 | 11/1996 | Weng et al. | 128/653.1 |
| 5,606,587 | 2/1997 | Barski et al. | 378/62 |
| 5,649,032 | 7/1997 | Burt et al. | 382/284 |
| 5,706,416 | 1/1998 | Mann et al. | 395/127 |
| 5,754,618 | 5/1998 | Okamoto et al. | 378/4 |
| 5,982,917 | 11/1999 | Clarke et al. | 382/132 |

*Primary Examiner*—David V. Bruce
*Attorney, Agent, or Firm*—Donald B. Paschburg

[57] ABSTRACT

A system for automatically composing target objects from a sequence of x-ray images for the purpose of diagnostic examination or measurement detects and matches semantically meaningful visual event hierarchy. The system can automatically composite the target object explicitly ignoring image regions that are not of interest for diagnosis. Diagnostic examination and measurement are helped significantly by the use of compound x-ray images. Prior to compound image generation, each constituent image undergoes two automatic pre-processing steps through a background detector and an emphasis field extractor. The system further includes a pair-wise aligner, a compound image generator and an examiner/measurer. The system increases the efficiency of compound image generation and improves its accuracy by de-emphasizing alignment of irrelevant structures in the images.

20 Claims, 9 Drawing Sheets

OBJECT

OUTSIDE THE APERTURE

DIRECT EXPOSURE

COLLIMATION

SYSTEM FOR GENERATING A COMPOUND X-RAY IMAGE FOR DIAGNOSIS

BACKGROUND OF THE INVENTION

1. Field of the Invention

The present invention relates to diagnostic x-ray imaging, and more particularly, to an x-ray imaging system that generates and displays a large compound image of a target object or structure by aligning smaller constituent images using semantic information extracted from the images.

2. Description of the Prior Art

In many diagnostic x-ray imaging situations, the target object to be imaged is much larger than the field of view of the imaging device. Even when it is possible to increase the field of view to cover the whole target object, the resulting image has insufficient resolution or possible geometric distortions in the off-center areas. It may also not be possible to cover the entire target object in one image because of the geometry or topology of the target object. It is nevertheless useful to present the entire target object in a single image to the human for the purpose of diagnosis. Moreover, it is important to compose the image with certain precision requirement for quantitative measurement in many clinical applications. For example, many musculoskeletal disorders such as scoliosis require the examination of the spine as a whole so that its geometry can be seen or measured. Due to the size of the spine, it is currently not possible to acquire a single x-ray image of the entire spine without adding significant distortions, deteriorating contrast or subjecting the patient to large x-ray doses. In present radiological practice, partial, overlapping constituent images are taken at several stations along the spine, starting from the back of the head down to the pelvis. The overlaps between the images can vary. The ability to view the entire object on a single image facilitates convenient and accurate diagnostic examination and measurement.

The traditional solution to this problem is to take a plurality of smaller x-ray images spanning the target object and manually assemble them into a larger whole. A human would line up two smaller images (films) by hand to identify the amount of overlap, cut one of the films to eliminate the overlap region on it and paste the two films together to form a larger image. Throughout this specification, the smaller images are referred to as images, to differentiate them from the larger, image. Adjacent constituent images are acquired with overlaps to facilitate later generation of the compound image.

There exist several prior art methods to mosaic constituent images into a larger whole, outside the realm of x-ray diagnostic imaging. Examples include U.S. Pat. No. 5,262,856 entitled "Video Image Compositing Techniques" issued on Nov. 16, 1993 and U.S. Pat. No. 5,649,032 entitled "System For Automatically Aligning Images To Form A Mosaic Image" issued on Jul. 15, 1997. Other examples are found in articles by P. Dani and S. Chaudhuri in "Automated Assembling Of Images: Image Montage Preparation", Pattern Recognition, vol. 28, no. 3, March 1995, pp. 431–445; by D. L. Milgram in "Computer Methods For Creating Photomosaics", Transactions on Computers, 1975, vol. 23, pp. 1113–1119 and by D. T. Pham, M. Abdollahi in "Automatic Assembly Of Ocular Fundus Images", Pattern Recognition, 1991, Vol. 24, No. 3, pp. 253–262. In x-ray diagnostic imaging, in addition to manual assembling of compound images, the prior art includes an automatic method to generate a compound image of the whole legs in peripheral angiography. This is described in U.S. Pat. No. 5,123,056 entitled "Whole-Leg X-Ray Image Processing And Display Techniques" issued on Jun. 16, 1992. U.S. Pat. No. 5,833,607 entitled "Automatic Full-leg Mosaic And Display For Peripheral Angiography", issued on Nov. 10, 1998 and assigned to the same assignees as the present invention also relates. U.S. Pat. No. 5,123,056 and U.S. Pat. No. 5,833,607 are hereby incorporated herein by reference.

When humans form compound diagnostic images manually, they make substantial use of visual knowledge of the target object or structures which are to be examined or measured in the compound image. However, few prior art automatic methods for image compositing extract or use semantic knowledge of the target object. Knowledge of semantically significant visual events in the constituent images, as well as knowledge about the purpose of compounding, can substantially improve the accuracy and efficiency of automatic image compositing. Explicit extraction and use of semantic knowledge for the purpose of diagnostic compound image generation is one object of the present invention.

SUMMARY OF THE INVENTION

This invention describes a method and apparatus that takes as input constituent x-ray images each of which contains a portion of a target object/structure, with each image overlapping at least one other image. The present invention automatically defines an emphasis field to emphasize the target object in each constituent image and uses this information to accurately and efficiently compose one compound image of the target object in its entirety from the constituent images. The compound image can be used for diagnostic examination or measurement using a computer ("soft-copy") display. Hard copies of compound images may also be used for diagnosis.

Prior to compound image generation, each constituent image undergoes two automatic pre-processing steps. These are through a background detector and an emphasis field extractor. The present invention further includes a pair-wise aligner connected to the emphasis field extractor and the background detector, a compound image generator and an examiner/measurer.

DETAILED DESCRIPTION OF THE INVENTION

Figure 1:
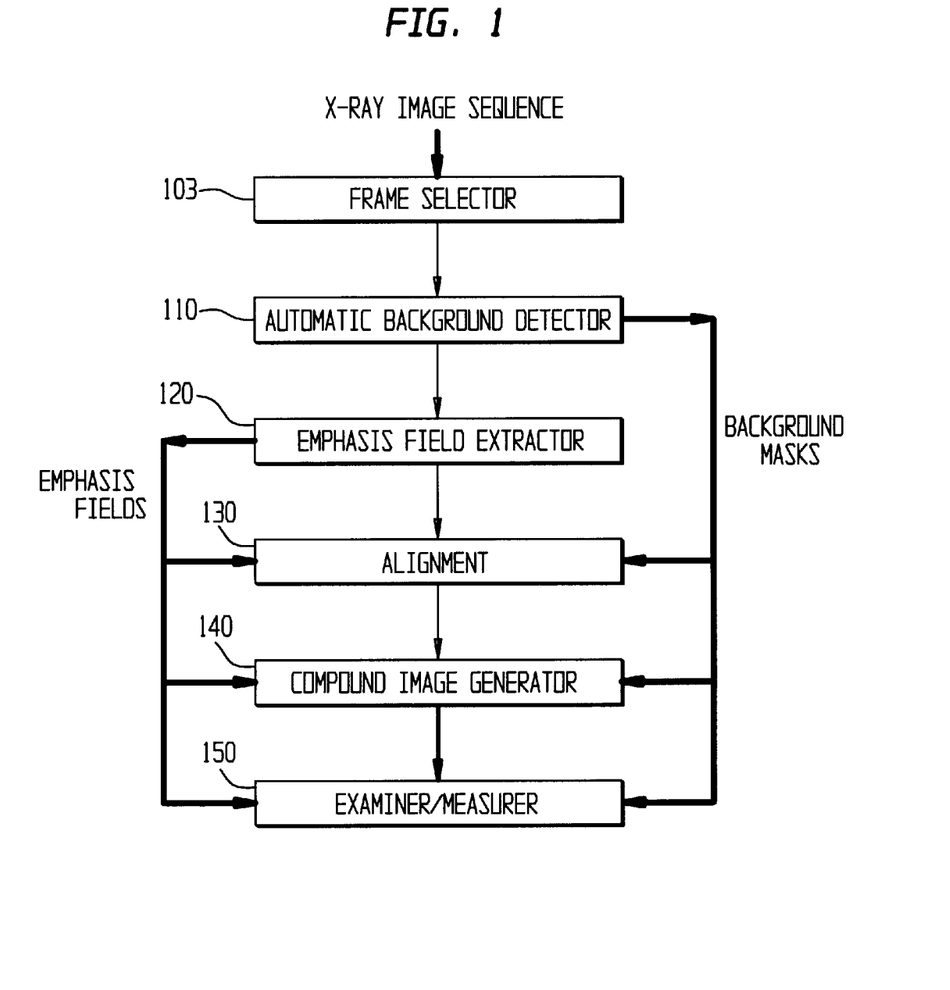
FIG. 1 illustrates a block diagram of the present invention.

A system for the generation and use of compound diagnostic x-ray images is shown in FIG. 1. The input to the system is a sequence of constituent x-ray images. Each image is taken at one "station" along the target object/structure and the images are to be combined into a single compound image.

The x-ray image sequence enters the system through frame selector 103 which will now be described. In some applications, image sequences rather than single images are acquired at each station. An example of this is peripheral angiography as described by T. Hilbertz, U. Fink, H. Berger, R. Beck and U. Eberwein in "Digital Peripheral Angiography With Subtraction And Stepping: Comparison With Other Techniques", Computer Applications in Radiology, Springer-Verlag, Berlin, pp. 62–67, 1991. A sequence of images is acquired at each of five to seven stations spanning the area between the pelvic region and the feet. In such applications, it is necessary to determine which single frame at each station is to be used for compound image generation. This analysis is performed in frame selector 103.

The present invention can incorporate manual, automatic or semi-automatic frame selection. An automatic method for frame selection is described by J-S. Chou, J. Qian, Z. Wu and H. Schramm in "Automatic Mosaic And Display From A Sequence Of Peripheral Angiographic Images", SPIE Medical Imaging, vol. 3034, 1077–1087, 1997, which analyzes the differences between successive frames and interprets large differences as station changes. Furthermore, this automatic method assumes that the final frame at each station shows the target structure (blood vessels) optimally and chooses this frame for compound image generation. The problem with this or other automatic methods for frame selection is that it is necessary to make assumptions about the order in which images appear in the subsequence at each station. Those familiar with the prior art are aware that a lot of variation in the order of images is typical. Even if it is known which frames belong to the same station, it is difficult to automatically and robustly determine which frame depicts the target organ/structure optimally. The problem is exacerbated if the same automatic frame selection method is to work across different diagnostic applications as with the present invention.

Figure 2:
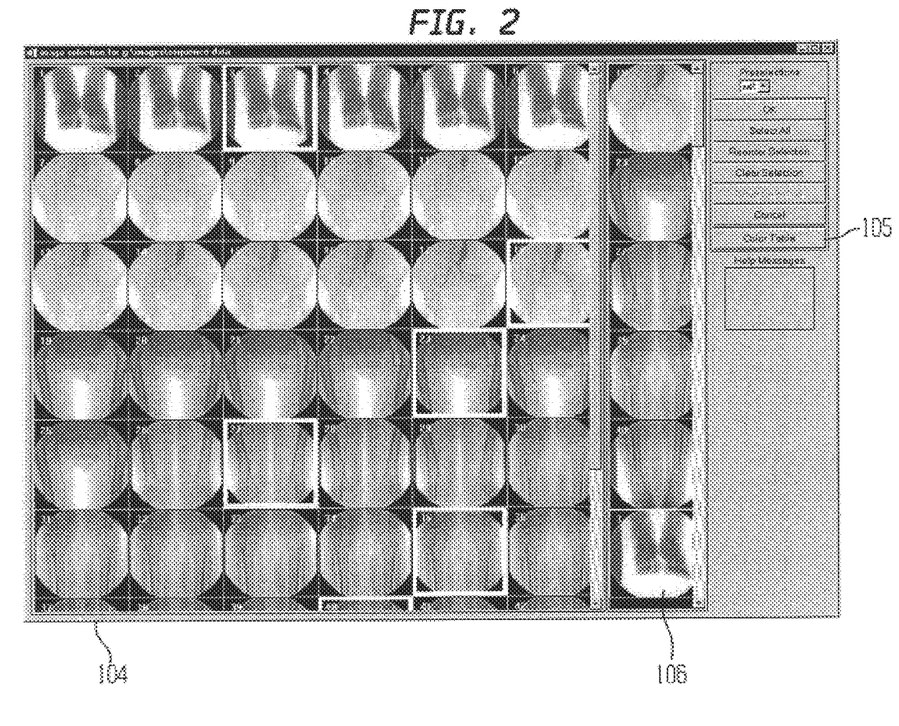
FIG. 2 shows an exemplary graphical user interface for manual frame selection.

FIG. 2 depicts an exemplary interface for manual frame selector 103. Image frames are shown to the human user as scaled down versions, or thumbnails 104. The user clicks on these thumbnails 104 to choose the frames to be used for compound image generation. The user also specifies the adjacency information for the constituent images 106. The system performs simple validation checks, such as ensuring that not more than one frame is chosen at each station, by analyzing frame differences. The primary responsibility of specifying the constituent images 106 and their adjacencies appropriately is with the human user. If the input directly consists of constituent images and not sequences, manual frame selection degenerates to specifying the adjacency information alone.

Prior to compound image generation, each constituent image undergoes two automatic pre-processing steps, namely through automatic background detector 110 and emphasis field extractor 120. These steps are described in detail below.

Figure 3A:
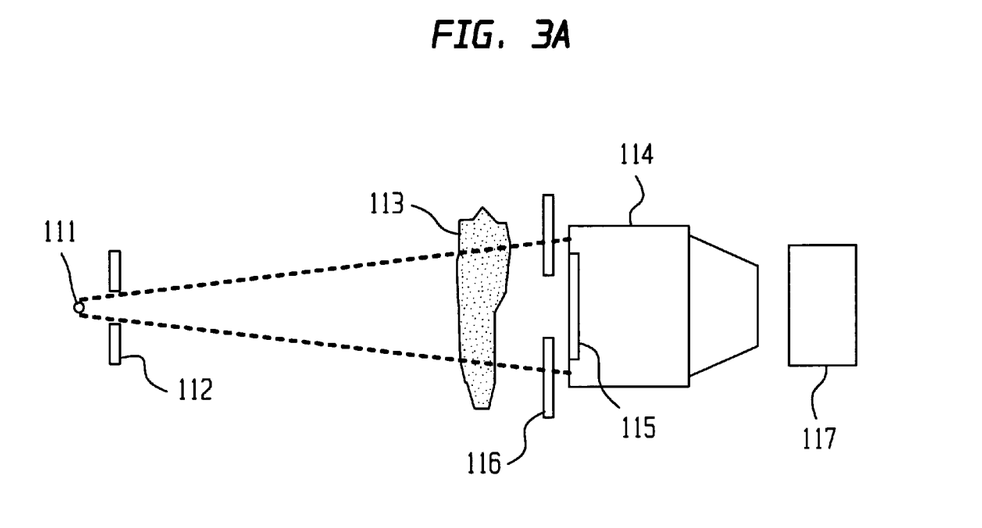
FIG. 3a illustrates an over-simplified schematic of a diagnostic x-ray image acquisition.
Figure 3B:
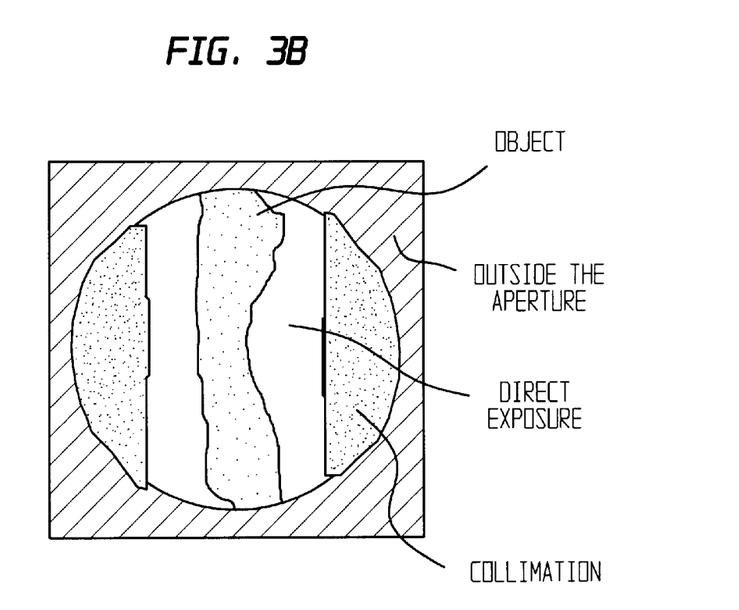
FIGS. 3b and 3c define "background" in an x-ray image.
Figure 3C:
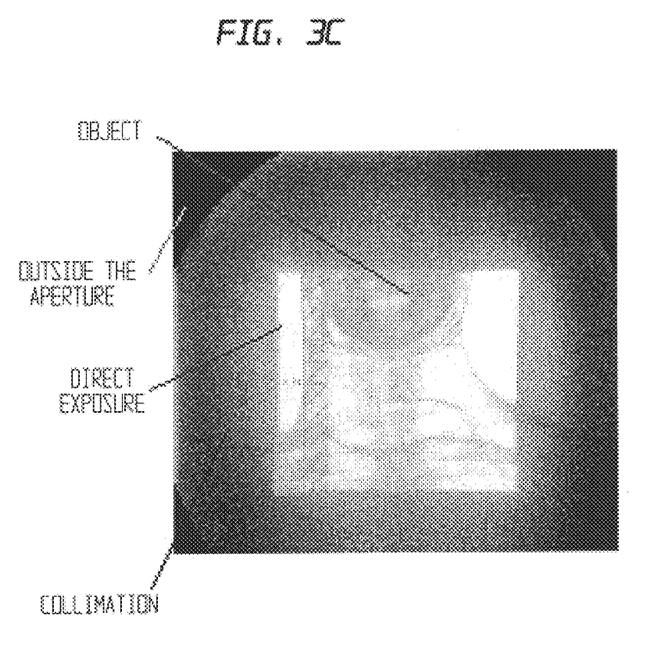

The following will describe automatic background detector 110. A peculiarity of diagnostic x-ray images is that often some image regions have negligible or no diagnostic content. Typically the object being imaged occupies only a portion of the image. Consider for example an oversimplified schematic of a diagnostic x-ray image acquisition shown in FIG. 3a. Rays from an x-ray source 111 pass through some beam-limiting devices (collimators) 112 before being incident on the body 113. The x-rays pass through the body 113, enter the image intensifier 114 through an aperture 115, after optionally going through another beam limiting device 116. The output of the image intensifier 114 is collected by a recording medium 117 such as a photographic plate or a TV camera. This imaging process can result in many background regions which are image regions with negligible or no semantic content. To illustrate background regions, FIGS. 3b and 3c, respectively, show a synthetic and a real x-ray image. (FIG. 3c is histogram equalized to clearly show the collimated region.) Background regions may include the following. 1. Totally dark regions outside the aperture, resulting from the fact that the size of the recording medium is typically larger than the aperture. 2. Regions in which x-rays are attenuated by collimators or other beam limiting devices. 3. Regions that receive unattenuated radiation because the body part may not span the whole area where x-rays are incident which is referred to commonly as direct exposure. 4. Saturation regions where if the strength of incident x-rays is higher/lower than the maximum/minimum strength the image intensifier or the recording medium can handle, the corresponding image area will have uniform intensity, even though the underlying object may have meaningful variations. It is common, though not necessary, for these "saturation" regions to occur in collimation or direct exposure regions in diagnostic x-ray images.

There may sometimes be external objects appearing in the image. In medical x-ray images, it is not unusual to see foreign objects such as catheters, measuring rulers, written characters or numbers, even physician's fingers. Such regions are not included in the definition of background because they are not semantically empty, just irrelevant. Emphasis field extractor 120 of FIG. 1 discounts such image regions by assigning them a small emphasis value.

Typically a significant portion of each constituent image is background. Detecting and eliminating background regions during compound image generation does generally alter the result, but does, however, have the following benefits. It improves the reliability of any adaptive thresholds the compounding algorithm may be using, for example for removing noise from the feature maps. It improves the efficiency of image alignment by reducing the number of possible alignments and search window sizes. It can help decrease the number of local maxima in the match criterion, which in turn could cause a false match. It improves the efficiency of image compositing by reducing the size of the overlap regions to be computed. It can improve the appearance of overlap regions in the compound image.

Figure 4:
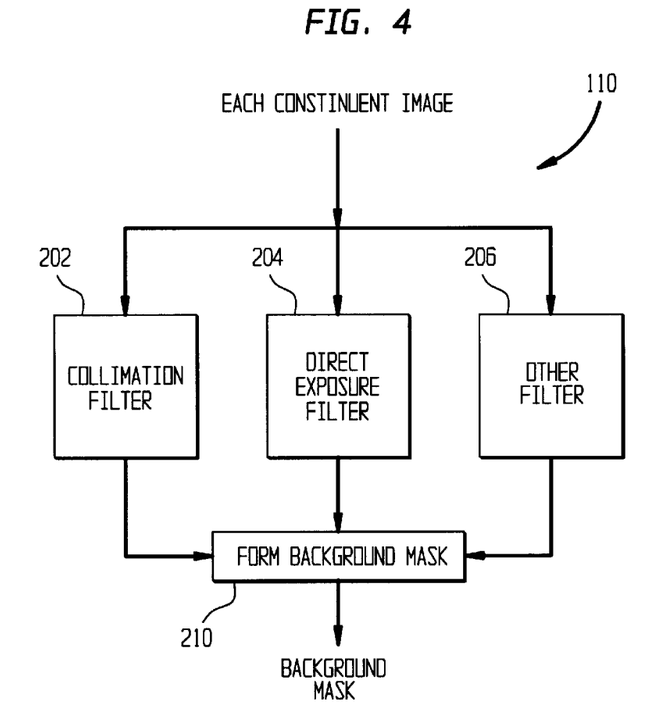
FIG. 4 illustrates a flow diagram of automatic background detection in x-ray images.

Automatic background detector 110 is described in detail in FIG. 4. Each constituent image is processed independently by background filters that detect collimation 202, detect direct exposure 204 and other types of background 206. Each filter outputs a binary mask in which the zero bits designate the background and the one bits designate the object. Outputs of all filters are combined to form background mask 210, e.g., through a logical OR operation, to form a single binary background mask for each constituent image.

The following will describe collimation detection filter 202. Collimation regions include image regions outside the aperture as well as regions that receive fully or almost fully attenuated radiation due to beam limiting devices (FIGS. 3b and 3c). Collimation regions typically have hardly any signal, so it is rather straightforward to detect them. There are prior art methods to detect collimation in x-ray images although not in the context of compound image generation. Examples are U.S. Pat. No. 4,970,393 entitled "Irradiation Field Recognizing Method And Method Of Adjusting Image Processing Conditions Using The Same" issued on Nov. 13, 1990 and U.S. Pat. No. 5,268,967 entitled "Method For Automatic Foreground And Background Detection In Digital Radiographic Images" issued on Dec. 7, 1993. These methods detect collimation accurately by analyzing intensity transitions as well as shapes of the collimator edges (circular arcs, straight lines).

For the present invention, it is necessary that collimation detection proceed very quickly, even at the expense of some accuracy. The following simple filter is used to detect rectangular collimation regions. The total intensity of pixels in each row is computed. In the resulting array, the absolute differences between successive elements are found. The system then finds the first and last elements where this difference is significantly large, i.e., more than an adaptive threshold which in turn is set based on the maximum and minimum differences. These elements correspond to the top and bottom rows of the non-collimation area. If none of the differences is larger than the adaptive threshold, it is inferred that there is no collimation in the vertical direction. The same procedure is repeated in the horizontal direction to detect the left and right borders of the non-collimation area.

The following will describe detect direct exposure filter 204. Direct exposure regions typically are the brightest in an image although this need not always be true. If there is semi-transparent collimation in the image, direct exposure regions may have a very similar appearance as some object regions. U.S. Pat. No. 5,268,967 described above and U.S. Pat. No. 5,606,587 entitled "Determination Of Direct X-ray Exposure Regions In Digital Medical Imaging" issued on Feb. 25, 1997, describe ways to detect direct exposure regions in medical x-rays assuming that they are the brightest parts of the image. An article by S. K. Murthy, J. Z. Qian, "Automatic Collimation For Peripheral X-ray Angiography", International Conference on Image Processing, Chicago, Ill., October 1998, and U.S. patent application Ser. No. 09/015,725 entitled "Method And Apparatus For Automatic Collimation In X-ray Peripheral Imaging" filed on Jan. 29, 1998 describe methods to automatically detect block collimation, bright direct exposure regions as well as some semi-transparent collimation from a medical x-ray image. With the present invention, any of the above prior art methods may be used to detect direct exposure.

For the detect other types of background filter 206, any efficient filter to detect saturation or other x-ray image regions having nil or negligible semantic content may be integrated into the present invention for automatic background elimination.

The second preprocessing step for constituent images is emphasis field extraction 120. An emphasis field of an image is a real array of the same size as the image, with pixel values in the range [0,1]. For example, the emphasis value at a pixel may designate the confidence/probability that the target object or structure is present at that pixel.

With automatic definition of a soft emphasis field for each constituent image, emphasis is highest on image regions most likely to contain the target object or parts of it. Depending on the target object, a human defines anatomic landmarks, semantically meaningful features on the image that give cues about the presence of the target object. The system automatically defines emphasis fields by detecting the presence of anatomic landmarks in the image.

The need for emphasis fields is as follows. Geometric and/or photometric distortions may imply that not all content in the constituent images may be used for image alignment or compositing. Regions corresponding to foreign objects with strong features (measurement rulers, text characters, etc.) which may confuse the alignment procedure or spoil the appearance of the composite image can be de-emphasized. Also, eliminating certain image areas from consideration improves the efficiency of compound image generation.

Figure 5:
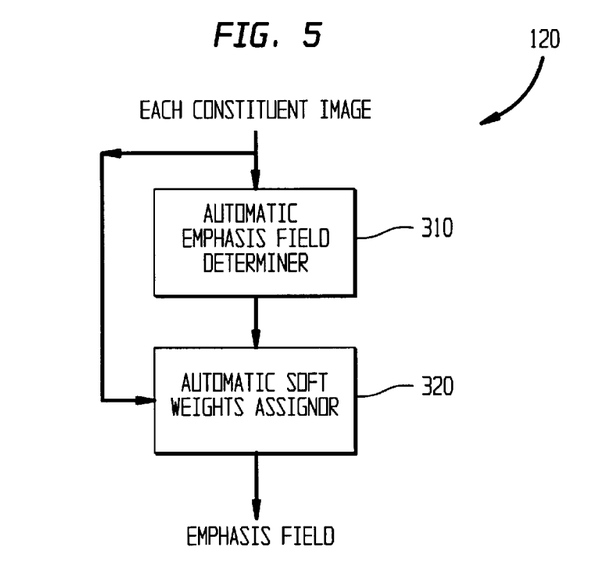
FIG. 5 illustrates a flow diagram of emphasis field extraction.

Several methods in the prior art use the concept of region of interest (ROI) for image processing. An emphasis field differs from a region of interest or focus of attention in that the former discourages sharp discontinuities. The emphasis field in any neighborhood in the image (except the background regions) varies smoothly. Emphasis fields are computed from automatically extracted ROI in automatic emphasis field determiner 310 and soft weights assignment 320, as shown in FIG. 5. The specific methods to define the ROI depend on the different applications. As the result of most automatic ROI detection methods may have some error, soft weighting the results increases the robustness. The emphasis fields are "soft" in nature, implying that non-zero weights are assigned to non-ROIs even though weights are highest where the target object is most likely to be present.

Important aspects of the emphasis field extraction of the present invention are the following. Automatically defining a "soft" weighting structure on the image pixels based on the automatically extracted ROI. Using emphasis fields explicitly while generating the compound image, to emphasize the target object regions and downplay or ignore the irrelevant regions. Using emphasis fields while displaying the compound image, for purposes like reducing the artifacts in the image and/or selectively visually enhancing the target object. The soft weight structure in an emphasis field for the same target object may be different at different stages of image compositing.

Figure 6:
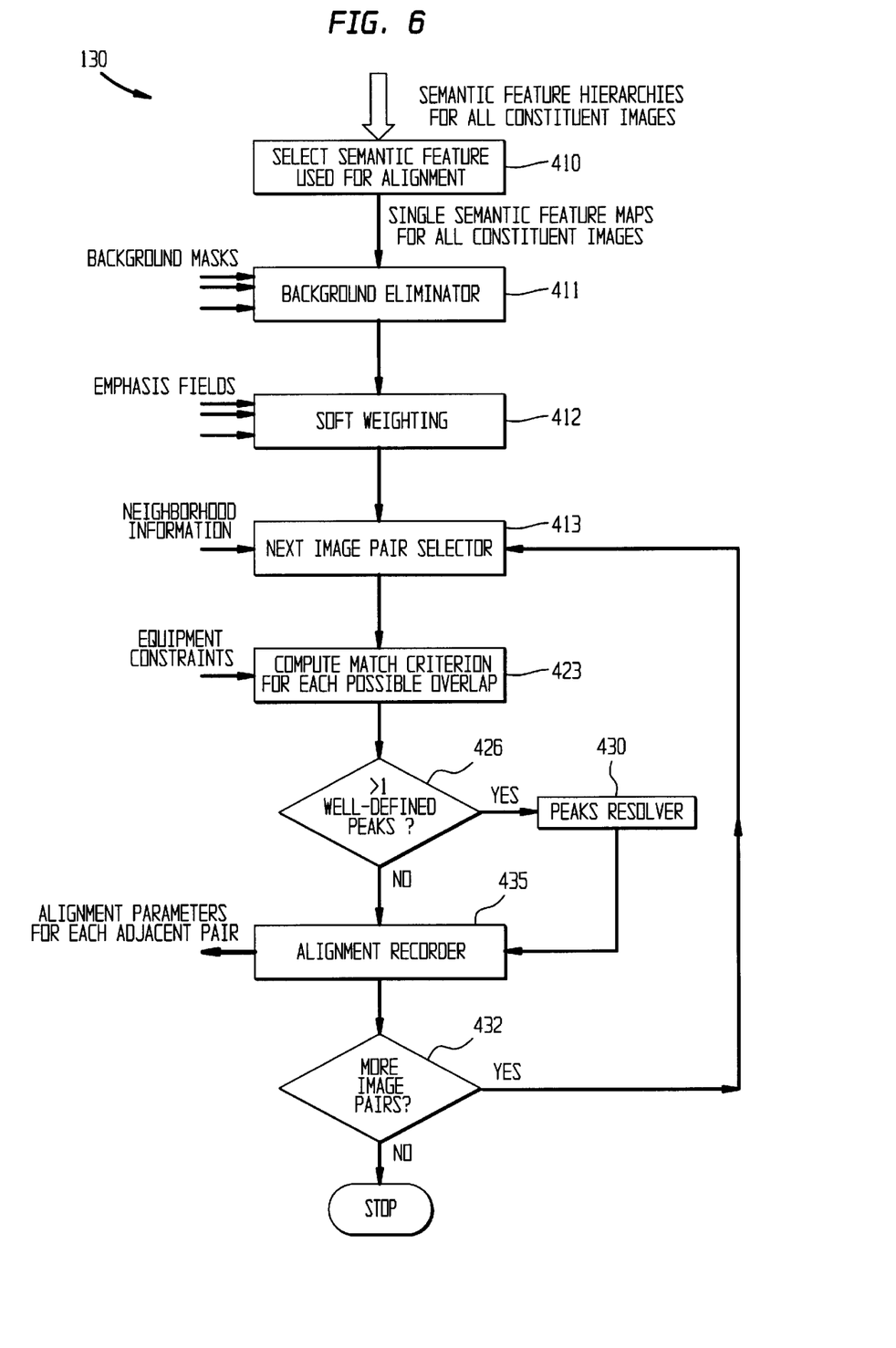
FIG. 6 illustrates a system for pair-wise alignment of a plurality of constituent images using semantic content.

FIG. 6 shows details of a system for pair-wise alignment of constituent images (130 of FIG. 1). Several methods for automatic image alignment for compound image generation exist outside the domain of diagnostic x-ray imaging. Some important works, both patents an technical articles, are cited in the Description of the Prior Art. Pair-wise image alignment methods typically proceed by moving one of the images to every possible overlap position on the other image, computing a match criterion for each overlap position and choosing the position corresponding to the best value of match criterion as the correct alignment between the images.

The present invention assumes that horizontal and vertical translations are the only possible transformations between adjacent constituent images. This restrictive assumption is made to improve the computational speed of alignment and to reduce the possibility of diagnostic artifacts. The use of emphasis fields for alignment alleviates to some extent the restrictiveness of this assumption. As diagnostic images are usually acquired by minimizing the distortions in the target object (e.g., by centering the image on the target object), concentrating on the target object during image compositing allows for using reduced complexity operators for image matching. For example, while aligning two images of the spine in the chest region, it may be necessary to geometrically distort or rotate the images in order to match all the ribs correctly. However, as the purpose of alignment is to examine the spine not the ribs, translatory transformations may be adequate once alignment in the spine region is emphasized much more than the ribs.

Some salient features of the alignment method used in the present invention are described below. The first is automatic elimination of background during image alignment by background eliminator 411. The number of possible overlap positions between two constituent images as well as the efficiency of alignment depend on the sizes of the images. As a significant portion of a constituent x-ray image is background which does not contribute towards alignment, eliminating background prior to alignment increases computational efficiency. Automatically computed background masks from automatic background detector 110 of FIG. 1 are used to eliminate background prior to alignment.

A second salient feature is aligning semantic features instead of pixels. Pixel intensity-based alignment methods are not robust to global changes in intensity which in turn are quite common in diagnostic x-ray imaging due to factors like external contrast enhancement agents, automatic gain control and varying object density. Gradient-based alignment methods avoid this problem but suffer from the fact that edges that do not have any semantic significance may adversely affect the alignment. To tackle these problems, the present invention extracts and uses semantically meaningful information such as directional topographic primal sketches to do the matching. The number of semantically meaningful feature pixels is much smaller than the number of intensity pixels or gradient pixels. This in turn implies efficiency as well as fewer false positives. The present invention uses the concept of a semantic feature hierarchy derived from emphasis field extractor of FIG. 5. The user manually chooses a particular feature to be used for matching from this hierarchy. This is identified by selector of semantic feature used for alignment 410 of FIG. 6. The advantage of using features at coarser stages of the semantic hierarchy for matching is computational efficiency whereas the advantage of using features at finer stages is precision.

A third feature of pair-wise alignment is soft feature weighting 412. Prior to computing the match criterion, feature pixels are weighted using the emphasis fields derived from emphasis field extractor 120 of FIG. 1. This is so that the match criterion reflects the alignment of the target regions/structures more strongly than it reflects the alignment of other image regions.

A fourth feature is that of match criterion (MC) computer 423. Given two image regions a and b of size m X n, the match criterion M of images a and b is defined as $$M(a,b) = \frac{\left(\sum_{(i+k,j+1)\in Sa}\sum_{(i,j)\in Sb}(MAX - |a(i+k,j+1) - b(i,j)| + (\max(a(i+k,j+1), b(i,j)))/(MAX+1))\right)}{(\sum_{(i+k,j+1)\in Sa} a(i+k,j+1) + \sum_{(i,j)\in Sb} b(i,j))}$$

where a(i+k,j+l) and b(i,j) are the feature values at pixel (i,j) of images a and b respectively. Variables k and l are translational shift variables. Variables $S_a$ and $S_b$ correspond to domains on which images a and b are defined (i.e., not background, not zero feature values). Value MAX is the maximum possible feature value. For example, if features are represented in a byte array, MAX is equal to 255. Feature values are assumed to be non-negative.

The process of alignment involves finding the particular overlap position at which M is maximized. (Cases where there are multiple peaks for the match criterion are addressed below.) The advantage of the above criterion over prior art methods is that perfect matches (matching a feature value against an identical value) are given maximum possible weight irrespective of the absolute strength of the feature. That is, perfect matches of strong features are weighted no more than perfect matches of weak features. This is important because there may be a lot of variation in the strength of semantically significant features in diagnostic images. In the absence of a perfect match, the above criterion weighs matches of stronger features more than matches of weaker features.

A new peak finding method for increasing the robustness of matching will now be discussed. After computing M at all possible overlap positions, its peak (maximum) value needs to be found. For robustness, all local maxima of M that are within a certain magnitude range of the global maximum are considered as candidate peaks. If there is only one candidate peak, the translational parameters corresponding to it are outputted as the alignment parameters for this pair. Alignment parameters for each adjacent pair are derived from recording the alignment corresponding to a peak performed in recorder 435 of FIG. 6. It is not unusual to have more than one candidate peak close to one another. Instead of arbitrarily choosing the largest peak as the correct one, the system executes an additional step to resolve the peaks. This is performed in well defined peak decider 426 and in resolver of peaks 430. The idea is that since the search space is now much smaller than the entire image, consisting of only a few candidate peaks, the system can afford to run the matching procedure using more complex features and/or more complex match criteria. The translation parameters corresponding to the candidate peak at which this more complex match criterion is maximized are outputted as the alignment parameters for this image pair.

To further improve the efficiency and robustness of the present invention, a multiscale search algorithm is used to find the best alignment between constituent images. A pixel pyramid is constructed for each constituent image. The alignment process starts with matching down-sized images at the coarsest pyramid level. The best alignment according to our matching criterion is computed and then propagated downward in the pyramid to match images of the next finer scale. This process is repeated until the full resolution images have been aligned. This multiscale search mechanism enables the system to use only small search windows for aligning fine scale images by centering the search windows at the position prescribed by coarse alignment. As a result, full resolution images can be aligned correctly without incurring the substantial computational cost associated with large search windows. This multi-scale approach also helps to reduce the likelihood of misalignment in cases where constituent images are noisy and/or suffer from mild geometric distortions. As images are downsized, the signal-to-noise ratio (SNR) increases and distortions become less appreciable.

Consequently, the images are more likely to align at the correct positions and the subsequent steps at finer resolutions will only refine those alignment positions. In addition, the use of a multiscale approach allows for the natural incorporation of information from the extracted semantic hierarchy which is inherently multiscale.

The above alignment procedure, through more image pairs decider 432, is repeated for each pair of adjacent images. The adjacency between images, known as neighborhood information, inputted to selector 413 of the next pair of images, is itself given by the user at the frame selector, 103 of FIG. 1, stage. In some diagnostic x-ray studies, the adjacency is well defined according to the constraints of the particular study being performed. For example, in peripheral angiography, the x-ray gantry moves in a straight line along the patient's legs from the pelvis region to the foot region. The neighborhood of each image consists of the image above and the image below, if any. Hardware equipment movement constraints inputted to computer of match criterion, 423 of FIG. 6, for each possible overlap may also be used to restrict the search space of possible overlaps. For example, a particular x-ray gantry may have upper and lower limits on the amount of overlap between successive stations. This can be used to avoid evaluating some overlap positions.

The following will describe compound image generator 140 of FIG. 1. The output of compound image generator 140 is the compound image. It may possibly be scaled to present the entire large object or structure on one screen to the user. It is important in most diagnostic applications to use a navigational (reduced) image in addition to the full resolution compound image. The reasons for this are the following. The full compound image is typically too large to fit on one screen. The navigational image gives the user an idea of the overall appearance of the target object or structure. For example, in scoliosis studies, seeing the full spine in one image helps the radiologist assess the curvature of the spine. The navigational image often enables the user to decide quickly which positions of the compound image are to be examined in full detail. Much of the compound image may be diagnostically uninteresting, so scrolling through several screens of the full-resolution compound image for identifying the interesting portions is cumbersome. Computing the full compound image may be inefficient in terms of processor and memory usage because the user may not need to look at most of it. It is more efficient to generate full resolution compound image areas as needed.

Figure 7:
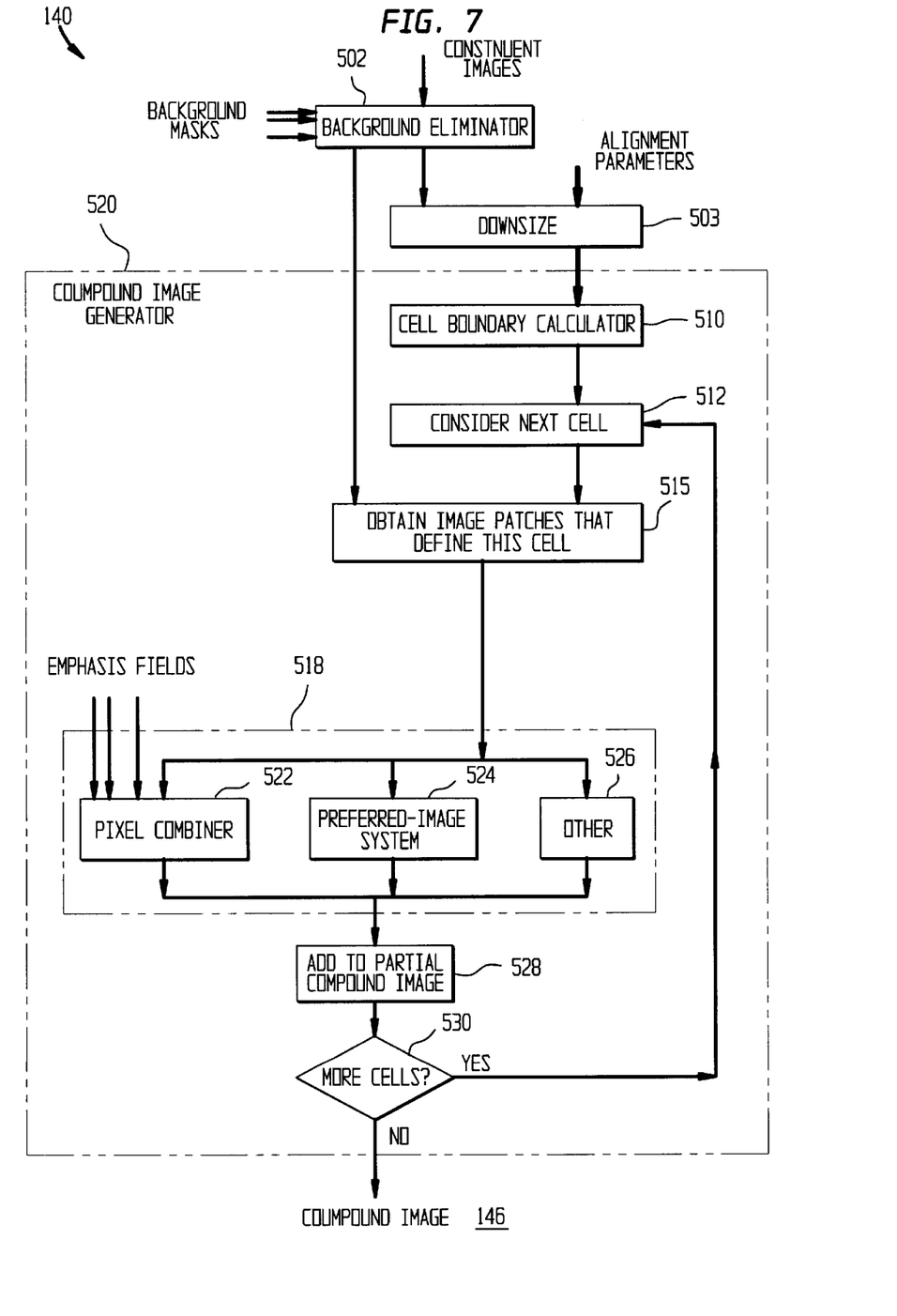
FIG. 7 illustrates a system for generating a compound image given a set of constituent images and their alignment parameters.

Of course, a navigational image by itself may not be adequate. Full resolution compound images are needed for accuracy of diagnostic measurement and liability issues. FIG. 7 shows a system for compound image generation 140 of FIG. 1. The first step is the elimination of the background through eliminator 502 in each constituent image using the background masks. Based on the available display size, a down-size factor is computed and the constituent images and alignment parameters are downsized in downsizer 503 accordingly. Default downsizing is no downsizing at all. The system then divides the image into cells, based on the alignment parameters and image sizes.

Figure 7A:
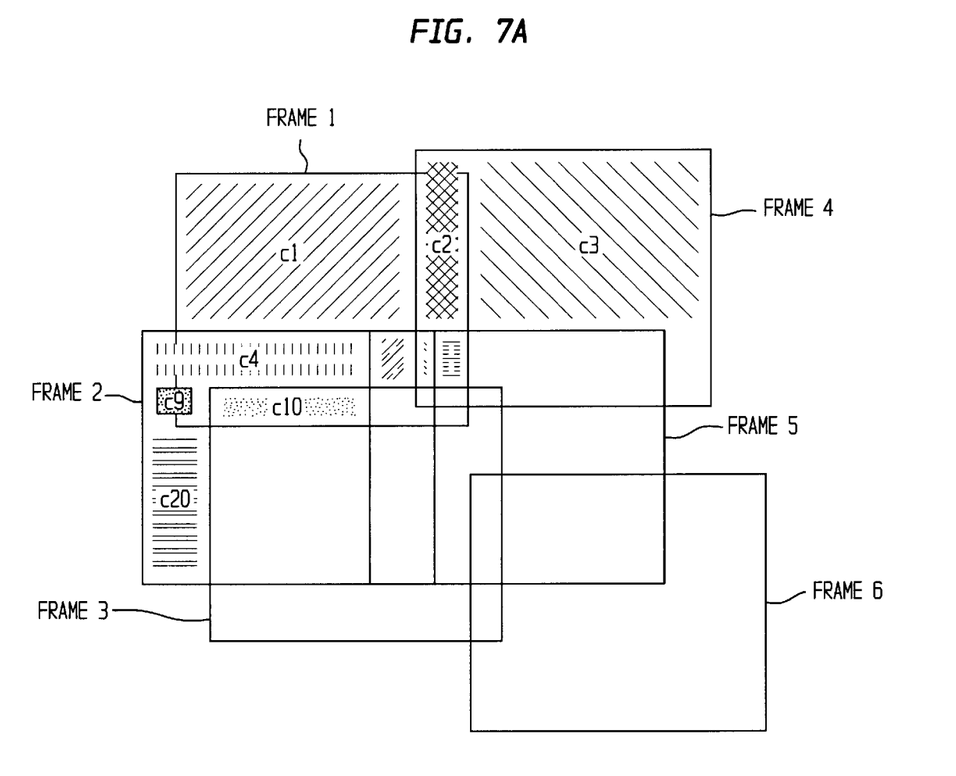
FIG. 7a shows how cells and their boundaries are defined on a compound image.
Figure 8:
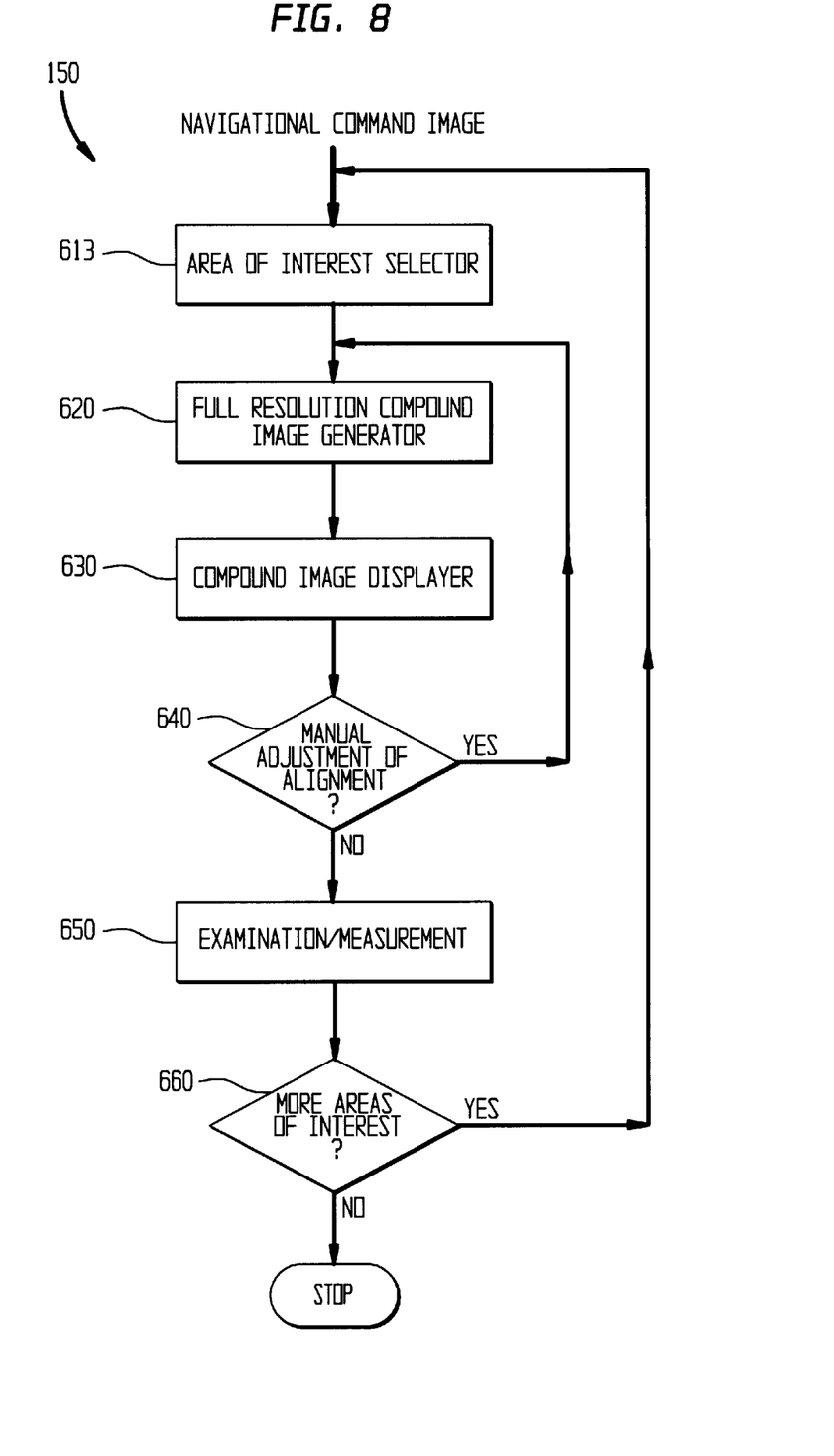
FIG. 8 illustrates a flow diagram of interactive diagnostic examination and measurement using compound images.

A cell is a part of the compound image and all pixels of the cell are computed from an identical set of constituent images. It is useful to divide the compound image into cells at the outset so that portions of the full resolution compound image can be computed efficiently on demand, for example in response to a manual adjustment of alignment parameters 640 of FIG. 8. Cells are also useful to keep track of which portions of the full resolution compound image have already been computed and which have not. Cell boundary calculator 510 in a case where adjacency is between vertically and horizontally neighboring pairs of images is illustrated in FIG. 7a. As neighborhood definition, inputted to choose next pair images 413 of FIG. 6, gets more complex, so does cell boundary calculation. Each cell has associated with it a ready flag. This flag is set when the cell is computed. Only the cells for which the flag is not set are recomputed at any time. Manual adjustment of alignment parameters for an image pair may result in the unsetting of the flags corresponding to the cells in their overlap region as well as some latter cells.

The primary task in compound image generation, navigational or full-resolution, is computing individual cells from multiple constituent images. The present invention through image combiner 518 incorporates several ways of combining image information which are described below. These methods are applied to compute each cell individually through cell boundary calculator 510 and consider next cell 512. Image patches corresponding to a cell derived from obtain image patches 515 of FIG. 7 are the relevant portions of the constituent images that overlap (see FIG. 7a) to form the cell.

One method to obtain image information is pixel combination using emphasis fields in pixel combiner 522 of FIG. 7. The emphasis field of a constituent image indicates which image regions are likely to contain the target object or structure and which are not. Since the purpose of the compound image is to examine the target object, it is appropriate to combine intensity values in image patches after weighing them by their emphasis fields. This is particularly useful if one or more of the image patches has little semantic information, say due to an imperfect background finding method.

A second method to obtain image information is the preferred-image system 524 of FIG. 7. The above method of combining may produce a visibly distracting pattern because each pixel value is calculated independently. An alternative is to compute some quality measure for each image patch and retain only the patch with the best value for the measure. Average intensity, average contrast, average value for emphasis field are some of the many possible quality measures that can be used to decide the preferred image patch.

A third method to obtain image information is shown as other image combiner 526 of FIG. 7. Methods have been explored in the prior art in which overlap regions are computed by weighted averaging of constituent image patches and varying the weights geometrically so that the seam between images is minimized. This is described by D. L. Milgram in "Computer Methods For Creating Photomosaics", Transactions on Computers, vol. 23, pp. 1113–1119, 1975. Weighted averaging can result in a blurred image, especially when the alignment parameters are imperfect. Seam removal in cases where more than two image patches make up a cell is not straightforward. Alternatively, one can divide a cell into as many equal sized parts as there are image patches corresponding to it and fill each part from one patch in some systematic order. This method has been referred to as clean cut merging by J-S. Chou, J. Qian, Z. Wu and H. Schramm in "Automatic Mosaic And Display From A Sequence Of Peripheral Angiographic Images", SPIE Medical Imaging, vol. 3034, pp. 1077–1087, 1997, where overlaps were restricted to at most two constituent images. When there are more than two image patches overlapping in a cell, one can use existing methods like the above after choosing the two "best" patches to combine, using some quality measure. After each cell region is computed independently, it forms the corresponding part of the compound image. This is performed in add to partial compound image 528. Through more cells decider 530, computation of individual cells is repeated until there are no more cells left.

The following will describe interactive diagnostic examinator/measurer 150 of FIG. 1. The system for interactive diagnostic examination and measurement using a compound x-ray image is summarized in FIG. 8. First the navigational compound image is presented to the user. The user examines this image and chooses an area of interest (AOI). AOI selector 613 by the user may be in terms of clicking a point of interest or drawing a box or free area on the image. In the case of clicking, the system adaptively determines an area around the point which is the AOI. The next step is to generate a full resolution compound image of the AOI in compound image of area generator 620. This step is very similar to compound image generator 520 of FIG. 7, except that this time (1) the compound image is generated at full resolution and (2) only the cell(s) spanning the AOI, not all possible cells, are considered. Once computed, the full resolution compound image is displayed, through compound image displayer 630, with clear indication of where in the navigational image it is from. After viewing the navigational or full resolution image, the user may decide that the automatically computed alignment parameters (FIG. 6) are incorrect. As the compound images are intended for diagnostic examination and/or measurement, precision in alignment is very important. It may thus be necessary to manually adjust and correct the alignment parameters. This is performed in manual adjustment of alignment 640. As the present invention allows only for translatory transformations, manual adjustment is implemented through horizontal and vertical slider bars. After all adjustments are made and the full resolution compound image appears satisfactory to the human, quantitative measurements may need to be made. This is performed in examination/measurement 650. The steps 613, 620, 630, 640 and 650 are repeated at different areas of interest 660 until the interactive examination/measurement are complete.

Figure 9:
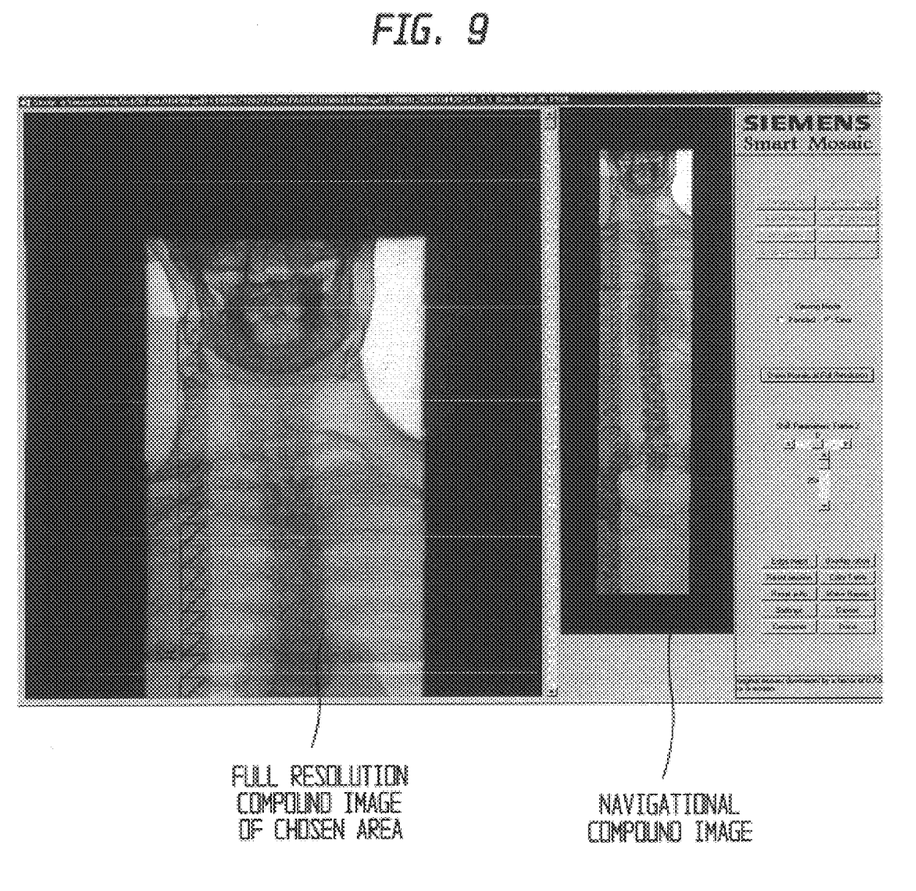
FIG. 9 shows an exemplary graphical user interface for using compound x-ray images for diagnosis.

The present invention provides a host of user interface tools for distance, area, intensity and other measurements from the compound image. An exemplary user interface to present compound images is shown in FIG. 9 where, generated by the present invention, a compound image of the human spine from a sequence of x-ray images is displayed. Initially only the navigational compound image is shown. As the user chooses areas of interest on the navigational image, corresponding portions of the full resolution compound image are (re)computed as necessary and displayed. Slider bars for manual adjustment of alignment parameters may also be noticed in FIG. 9.

It is not intended that this invention be limited to the hardware or software arrangement, or operational procedures shown disclosed. This invention includes all of the alterations and variations thereto as encompassed within the scope of the claims as follows.

What is claimed is:

1. A system for generating a compound x-ray image for diagnosis comprising:
   a background detector;
   an emphasis field extractor connected to said background detector;
   a pair-wise aligner connected to said emphasis field extractor and said background detector;
   a compound image generator connected to said pair-wise aligner, said background detector and said emphasis field extractor; and
   an examiner/measurer connected to said navigational compound image generator for providing said compound x-ray image.

2. A system for generating a compound x-ray image for diagnosis as claimed in claim 1 further comprising:
   a frame selector.

3. A system for generating a compound x-ray image for diagnosis as claimed in claim 1 wherein said background detector comprises:
   a background filter; and
   a background mask former connected to said background filter.

4. A system for generating a compound x-ray image for diagnosis as claimed in claim 3 wherein said background filter comprises:
   a collimation filter;
   a direct exposure filter; and
   other filters for detecting background.

5. A system for generating a compound x-ray image for diagnosis as claimed in claim 3 wherein said background filter comprises:
   a collimation filter; and
   a direct exposure filter.

6. A system for generating a compound x-ray image for diagnosis as claimed in claim 3 wherein said background filter comprises:
   a collimation filter.

7. A system for generating a compound x-ray image for diagnosis as claimed in claim 3 wherein said background filter comprises:
   a direct exposure filter.

8. A system for generating a compound x-ray image for diagnosis as claimed in claim 1 wherein said emphasis field extractor comprises:
   an emphasis field determiner; and
   an automatic soft weights assignor connected to said emphasis field determiner.

9. A system for generating a compound x-ray image for diagnosis as claimed in claim 1 wherein said pair-wise aligner comprises:
   a background eliminator;
   soft weighting connected to said background eliminator;
   a next image pair selector connected to said soft weighting;
   a match criterion computer connected to said next image pair selector;
   a well defined peaks decider connected to said match criterion computer;
   a peaks resolver connected to said well defined peaks decider;
   an alignment recorder connected to said well defined peaks decider and said peaks resolver; and
   a more image pair decider connected to said alignment recorder and said next image pair selector.

10. A system for generating a compound x-ray image for diagnosis as claimed in claim 9 wherein said match criterion computer comprises:
    calculation means for calculating match criterion according to $$M(a,b) = \frac{\left( \sum_{(i+k,j+l) \in S_a} \sum_{(i,j) \in S_b} (\text{MAX} - |a(i+k,j+1) - b(i,j)| + (\max(a(i+k,j+1), b(i,j)))/(\text{MAX}+1)) \right)}{(\sum_{(i+k,j+l) \in S_a} a(i+k,j+1) + \sum_{(i,j) \in S_b} b(i,j))}$$

where M(a,b) is match criterion of images a and b, a(i+k,j+l) and b(i,j) are feature values at pixel (i,j) of images a and b respectively, variables k and l are translational shift variables, variables $S_a$ and $S_b$ correspond to domains on which images a and b are defined and value MAX is maximum possible feature value.

11. A system for generating a compound x-ray image for diagnosis as claimed in claim 1 wherein said compound image generator comprises:

a background eliminator;

a cell boundary calculator connected to said background eliminator;

a consider next cell decider connected to said cell boundarly calculator;

an image patch obtainer connected to said background eliminator and said consider next cell decider;

an image combiner connected to said image patch obtainer;

an adder connected to said image combiner; and a more cell decider connected to said adder and said consider next cell decider.

12. A system for generating a compound x-ray image for diagnosis as claimed in claim 11 wherein said image combiner comprises:

a pixel combiner connected between said image patch obtainer and said adder.

13. A system for generating a compound x-ray image for diagnosis as claimed in claim 11 wherein said image combiner comprises:

a preferred image system connected between said image patch obtainer and said adder.

14. A system for generating a compound x-ray image for diagnosis as claimed in claim 1 wherein said compound image generator comprises:

a navigational compound image generator.

15. A system for generating a compound x-ray image for diagnosis as claimed in claim 14 wherein said navigational compound image generator comprises:

a downsizer; and a compound image generator connected to said downsizer.

16. A system for generating a compound x-ray image for diagnosis as claimed in claim 1 wherein said examiner/measurer comprises:

an area of interest selector;

a full resolution compound image generator connected to said area of interest selector;

a compound image displayer connected to said full resolution compound image generator;

a manual adjustment decider connected to said compound image displayer and said full resolution compound image generator;

an examination/measurement device connected to said manual adjustment decider; and a more areas of interest decider connected to said examination/measurement device and said area of interest selector.

17. A method for generating a compound x-ray image for diagnosis comprising the steps of:

detecting background regions of a constituent image;

extracting emphasis field of said constituent image;

performing pair-wise alignment;

generating a compound image; and performing interactive diagnostic examining and measuring.

18. A method for generating a compound x-ray image for diagnosis as claimed in claim 17 further comprising the step of:

selecting a frame.

19. A method for generating a compound x-ray image for diagnosis as claimed in claim 17 wherein performing pair-wise alignment comprises the steps of:

selecting a semantic feature used for alignment;

eliminating background;

soft weighting;

selecting a next image pair;

computing match criterion for each possible overlap;

deciding if well-defined peaks exist;

resolving peaks;

recording alignment; and deciding if more image pairs.

20. A method for generating a compound x-ray image for diagnosis as claimed in claim 17 wherein generating a compound image comprises the steps of:

eliminating background;

calculating a cell boundary;

considering a next cell;

obtaining image patches that define a cell;

combining images;

adding a combined image to a partial compound image; and deciding if there are more cells.

* * * * *